United States Patent
Brown (10) Patent No.: US 7,338,475 B2
(45) Date of Patent: Mar. 4, 2008

(54) ELECTRET ENHANCED AUTOMATIC IV DRIP CHAMBER SHUTOFF

(75) Inventor: Houston Brown, Poway, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 319 days.

(21) Appl. No.: 11/016,280

(22) Filed: Dec. 17, 2004

(65) Prior Publication Data
US 2006/0135939 A1 Jun. 22, 2006

(51) Int. Cl.
A61M 5/00 (2006.01)

(52) U.S. Cl. ..................................... 604/246
(58) Field of Classification Search ............... 604/246, 604/247, 127, 500; 137/433; 251/65, 129.01
See application file for complete search history.

(56) References Cited

U.S. PATENT DOCUMENTS

| | | | |
|---|---|---|---|
| 3,207,372 A | 9/1965 | Evans | |
| 3,731,670 A | 5/1973 | Loe | |
| 3,850,189 A | 11/1974 | Follett | |
| 4,005,724 A | 2/1977 | Courtot | |
| 4,038,981 A | 8/1977 | LeFevre et al. | |
| 4,344,004 A | 8/1982 | Okubo | |
| 4,465,095 A | 8/1984 | Lindberg | |
| 4,489,863 A | 12/1984 | Horchos et al. | |
| 4,585,209 A | 4/1986 | Aine et al. | |
| 4,732,162 A | 3/1988 | Martell | |
| 5,019,723 A | 5/1991 | Tran | |
| 5,118,046 A | 6/1992 | Tholander | |
| 5,280,806 A | 1/1994 | Glazebrook | |
| 5,423,346 A * | 6/1995 | Daoud | 137/399 |
| 5,468,142 A | 11/1995 | Koziol | |
| 5,527,295 A | 6/1996 | Wing | |

(Continued)

FOREIGN PATENT DOCUMENTS

DE  92 05 173.1 U1  8/1992

(Continued)

OTHER PUBLICATIONS

G. Sessler, ed.; "ELECTRETS, 3rd edition, vol. 1," *Electrostatic Source Book Catalog*, pp. 1-2, http://www.electrostatic.com/Sessler.htm.

(Continued)

Primary Examiner—Manuel Mendez
(74) Attorney, Agent, or Firm—McDermott Will & Emery (57) ABSTRACT

An automatic stop valve formed in a container of a medical fluid administration system includes an electrical field that attracts the float and valve seat together to shut off flow from the exit port of the container when the fluid within the container is reduced to a predetermined level. One or both of the float and valve seat creates an electric field that attracts the other, which is made of a non-magnetic dielectric, into engagement. In one embodiment, the valve seat is formed of an electret that creates the electric field attracting the float to it to stop flow. In another embodiment, the float comprises an electret that attracts the float to the dielectric valve seat. In yet another embodiment, both the float and valve seat include electrets of opposite polarity that attract each other into engagement. The lack of magnetic and metallic materials makes the shut off valve suitable for use in an MRI environment.

24 Claims, 6 Drawing Sheets

U.S. PATENT DOCUMENTS

| | | | | |
|---|---|---|---|---|
| 5,660,205 | A | * | 8/1997 | Epstein .................. 137/512.15 |
| 6,095,189 | A | | 8/2000 | Ben-Shalom |
| 6,120,002 | A | * | 9/2000 | Biegelsen et al. ..... 251/129.01 |
| 6,195,012 | B1 | | 2/2001 | Yang |
| 6,213,986 | B1 | * | 4/2001 | Darling, Jr. .................. 604/248 |
| 6,402,309 | B1 | | 6/2002 | Litman |
| 6,676,106 | B2 | * | 1/2004 | Swartz et al. .......... 251/129.01 |
| 6,695,004 | B1 | * | 2/2004 | Raybuck ..................... 137/433 |
| 6,855,126 | B2 | * | 2/2005 | Flinchbaugh ............... 604/106 |
| 2002/0143292 | A1 | | 10/2002 | Flinchbaugh |
| 2002/0182091 | A1 | | 12/2002 | Potter |

FOREIGN PATENT DOCUMENTS

| | | |
|---|---|---|
| DE | 43 19 115 A1 | 12/1994 |
| EP | 0 250 948 A2 | 1/1988 |
| WO | WO 2004/060457 A1 | 7/2004 |

OTHER PUBLICATIONS

R. Gerhard-Multhaupt ed.; "ELECTRETS, 3$^{RD}$ edition, vol. 2,"*Electrostatic Source Book Catalog*, pp. 1-5, http://www.electro-static.com/gerhardmult.htm.

N.J. Hermanson et al., "Syndiotactic Polystyrene: A New Polymer for High-Performance Medical Applications," 1988 Medical Plastics and Biomaterials, pp. 1-7.

A.M. Sabatini et al., "A system for measurement of surface charge densities on tubular electrets,"1990 Meas. Sci. Technol. 1, pp. 1099-1101.

International Search Report—International Application No. PCT/US2005/044763; International Filing Date: Dec. 9, 2005; (Earliest) Priority Date: Dec. 17, 2004.

* cited by examiner

ELECTRET ENHANCED AUTOMATIC IV DRIP CHAMBER SHUTOFF

BACKGROUND OF THE INVENTION

The invention relates generally to medical fluid flow valves and more particularly, to valves that automatically shut off when fluid reaches a certain level.

During hospitalization, a physician may desire to infuse a medical fluid into a patient's bloodstream. The medical fluid may be for therapy, the replacement of body fluid, or for other purposes. During the administration of medical fluids to a patient, it is important to avoid the infusion of air in amounts exceeding a certain quantity threshold. If too large a quantity of air is allowed to enter the patient's blood stream, an embolism could result, which can be a serious condition.

In infusing medical fluids, many times a medical fluid reservoir, such as a bag or bottle, is hung in an inverted position and its contents are allowed to infuse into the patient either through gravity or with the aid of an infusion pump that accurately controls the flow rate in accordance with programmed instructions. A fluid administration set is used to conduct the fluid from the bag to the patient and comprises a fluid line that is connected to the inverted bag at one end, referred to as its proximal end or upstream end, and is connected to a catheter inserted into the vein of a patient at the other end, referred to as its distal end or downstream end.

Many fluid infusion administration sets include a device known as a drip chamber. This device may include a sharpened spike at its upstream end for penetrating the stopper or septum of the reservoir, which may take the form of an inverted bag, bottle, or other type of container, to gain access to the contents of that container. The spike has a length that extends into the fluid of the reservoir and consequently conducts the contents of the reservoir to a precise drop former located at its inlet or upstream end of the drip chamber. The drop former forms drops having a known quantity of liquid that fall to the downstream end of the drip chamber due to gravity. The drops may be counted per unit of time to determine the flow rate of fluid into the patient. The drop former is located within the chamber of the drip chamber and at the downstream end of the chamber, in which the formed drops fall or "drip," an outlet exists that connects to the tubing of the administration set. That tubing provides a conduit for the medical fluid to flow to the patient.

Nurses monitor the drip chamber for the presence of drops to be sure that the medical fluid reservoir has not emptied. As is well known to those skilled in the art, drip chambers are designed to continuously have a certain level of fluid within the chamber when the flow of fluid into the patient is proceeding normally, such as 3 ml. When the fluid in the reservoir and tube above the drip chamber is exhausted and drops cease to fall, the level of fluid in the drip chamber will decrease until eventually it is empty. Unless the administration set tubing is clamped or other action is taken, air may then enter the administration tubing to which the drip chamber is connected. Thus, an empty fluid reservoir may result in air being drawn into the drip chamber and tubing and consequently being infused into the patient unless the line is clamped or other action is taken.

Additionally, if the fluid level in the drip chamber is permitted to decrease too far, the nurse cannot replace the empty fluid reservoir with a full reservoir unless the entire administration set is primed again to remove air that has found its way into the line. Priming the line takes time and it is desirable to provide devices that control the entry of air into the fluid line so that the procedure of re-priming is not necessary. In particular, it is desirable that enough fluid remain in the drip chamber when the present reservoir is exhausted so that a new fluid reservoir may be connected to the drip chamber and the flow of new fluid to the patient begin without the need for re-priming the fluid administration set.

In another application, the drip chamber may form a part of a burette and be located at the distal, or downstream, end of the burette chamber. In such a case, the drip chamber would not include a sharpened spike but would include the other elements discussed above. In yet a further arrangement, the drip chamber may not have a spike but may instead be fed at its upstream end by a length of tubing that has an integral spike for establishing communication with the container of medical fluid. The spike on the tubing is inserted into the reservoir and the fluid flows through the short length of tubing into the drip chamber.

It is desirable to provide a device that automatically shuts off flow when the medical fluid reservoir becomes depleted. Therefore, those in the development of medical fluid infusion devices have created various shut off valves that have been incorporated directly into the drip chamber device to automatically shut off fluid flow through the fluid line once the medical fluid reservoir has emptied. Some of these systems are relatively complex while some are simpler. One class of such devices uses a device that floats in the liquid of the drip chamber and has a valve seat located at the downstream end of the drip chamber. As is typical in these designs, the floating device floats at a certain level in the fluid dependent upon the buoyancy of the floating device. The floating device is designed to seat when the fluid in the chamber decreases to a certain low level. As the level decreases, the float approaches nearer and nearer the valve seat until it finally seats and shuts off flow thereby providing an automatic shut off valve that does not require constant monitoring.

Problems have arisen with such devices, one of which is that the floating device may not properly seat and completely shut off flow. Under adverse conditions, such as where the administration set may be moving from side to side or oriented at an angle other than directly vertical, the valve device may be slow in seating and fluid shut off may be delayed, thus raising the possibility that air may enter the administration line. Another adverse condition that arises is when a pump operating at a low flow rate is engaged with the fluid line and is creating pulses in the fluid upstream that tend to bounce the floating device away from the valve seat. These pulses may be strong enough to overcome the gravitational force on the floating device and it may not seat when desired.

A variation in this type of automatic shut off valves has incorporated magnetic force to assist in fluid line shut off. The force of magnetic attraction is used between a float located in the drip chamber and a stationary part, such as a valve seat, to shut off fluid flow in the administration line. Such an approach has an advantage in that it acts as a latching-type of valve. That is, the magnetic field or fields used have a field strength that increases non-linearly as the distance between the magnetic devices decreases. While some attraction exists when the magnetic devices are relatively far apart from each other, that attraction increases as they near each other until finally, the magnetic force provided by their attraction overcomes the buoyancy of the float in the drip chamber and it is drawn into a seating position in this magnetically activated valve thus positively shutting off fluid flow.

This magnetic force developed between the two parts tends to hold the valve in the closed or shut off position better than other valves that rely only on gravity. Where prior floats relied only on their weight to seal the fluid line, the use of a magnetic force as well as the weight of the float result in a better chance that the float will completely seal and shut off flow before air enters the fluid line. The use of a magnetic force also tends to draw the float into the seat when the drip chamber is tilted out of vertical alignment. Once seated, the valve is "latched" in that some mechanical force beyond that provided by the mere buoyancy of the float developed by newly added fluid is required to separate the float from its valve seat. Even filling the drip chamber with fluid will typically not dislodge the float from the valve seat in these devices. The force of the magnetic attraction to the seat exceeds the force provided by the buoyancy of the float and some mechanical force is necessary to dislodge the two. Typically, the wall of the drip chamber needs to be squeezed to dislodge the float from the valve seat so that it may rise to the level of the fluid.

While the use of magnetism in drip chambers has been an improvement in the art, certain magnetic devices have drawbacks. Magnetic devices comprising metallic elements should not be exposed to medical fluid in the infusion line. Additionally, some prior devices have uniquely shaped float devices that must be installed in a particular orientation in the drip chamber as the device is manufactured. Failure to properly orient the parts during manufacture can result in a valve that does not completely seal and may therefore need to be scrapped. Such requirements increase manufacturing costs. In other devices, the seal is formed between relatively rigid surfaces, and this configuration may give rise to the problem of leakage at the seal due to imperfections, or lack of fit, between the sealing surfaces. In yet another arrangement, the two devices comprising the valve, at least one of which is a magnet, may not be aligned so that the lines of magnetic flux between the two devices are then not optimally effective. In such a case, a larger magnet is used, which can increase costs. Magnetic shutoff valve devices are further subject to other troubles. The valvets emission of a magnetic field may negatively affect things such as whole blood containing iron. Also, strong external magnetic fields may influence the valve seal, either causing premature occlusion or preventing sealing when it is needed. Moreover, a magnetic shutoff valve device would not be suitable in an MRI environment, thus limiting its range of applications.

Hence, a need has been recognized by those skilled in the art for an automatic shut off valve usable in fluid administration lines that is efficient and reliable in operation. A need has also been recognized for an improved automatic fluid shut off valve that uses an attractive force between valve elements to result in a more dependable shut off action of the valve yet, does not interfere with the components of medical fluids, blood, or an MRI environment, or other medical environment. Yet a further need has been recognized for a fluid shut off valve that is relatively easy to manufacture and has lower manufacturing costs. The present invention fulfills such needs and others.

INVENTION SUMMARY

Briefly and in general terms, the present invention is directed to an apparatus and method for a shut off valve used in a medical apparatus which includes an attractive force between the valve components generated by non-magnetic and non-metallic materials. In a further detailed aspect, an electrical field is provided that attracts the components together to shut off flow. In yet a further more detailed aspect, at least one of the components produces an electrical field and the other component is formed of a dielectric that is attracted to the electrical field so that the two components attract each other for engagement to shut off flow. In yet another detailed aspect, the electrical field is produced by a component that is an electret. In yet another detailed aspect, the electrical field is produced by a component that is a ferroelectric polymer.

In further detailed aspects in accordance with the invention, there is provided an automatic shut off valve for use in regulating the flow of medical fluid. In one aspect, an automatic shut off valve for use in regulating the flow of medical fluid comprises a container adapted to contain medical fluid, with the container having an upstream end and a downstream end and defining an exit orifice at the downstream end. A stop member or float that may resemble a sphere or ball is disposed within the container. There is also a valve seat located proximate the exit orifice at the downstream end of the container. At least one of the float and valve seat produces an electrical field while the other of the float and valve seat is made of a dielectric that is attracted by the electrical field and tends to move into engagement with the other to stop flow. In a further more detailed aspect, both the float and the valve seat create electrical fields that are opposite in polarity and thereby attract each other into engagement to shut off flow. In a further aspect, the attraction created between the components has strength to overcome the buoyancy of the float in the medical fluid when a predetermined quantity of medical fluid remains in the container thereby shutting off flow.

In more detailed aspects, the component creating the electrical field has an electrical charge permanently affixed within its bulk. In another aspect, the component creating the electrical field has an electrical charge permanently affixed at its surface. In the case where the other of the float or valve seat does not create an electrical field, it is formed of a nonpolar polymer that is attracted by the electrical field. In another aspect, the component creating the electrical field comprises an electret. In yet another detailed aspect, the material creating the electrical field comprises a ferroelectric polymer.

In yet a further aspect, the component creating the electrical field is physically isolated from any medical fluid flowing through the container by covering the component with a biologically inert substance. In another detailed aspect, the component creating the electrical field is coated with Parylene™ or other water resistant material. In yet a further more detailed aspect, the diameter of the stop member and its buoyancy are selected to control the quantity of fluid remaining in the drip chamber when the automatic valve shuts off flow.

In yet another more detailed aspect, the strength of the electrical field produced by one or more of the components is selected so that the components will attract the float and the valve seat together for shutting off flow when a selected level of fluid remains in the drip chamber. Furthermore, the strength of the electrical field is selected so that the stop member will more readily align itself with the valve seat for automatic shutoff when the container is disposed at an angle other than vertical.

Other features and advantages of the present invention will become more apparent from the following detailed description of the invention when taken in conjunction with the accompanying drawings.

DETAILED DESCRIPTION OF THE PREFERRED EMBODIMENTS

Figure 1:
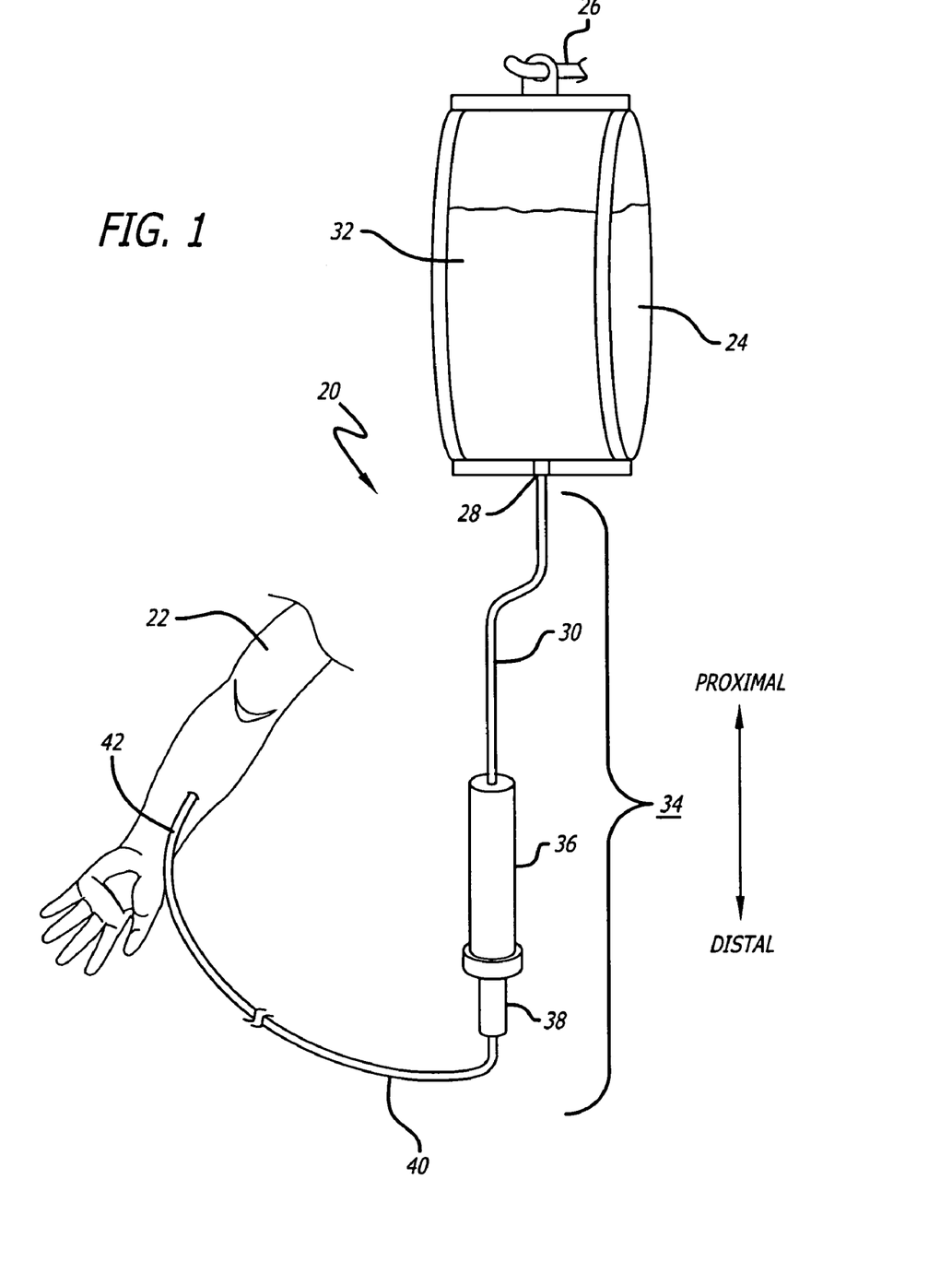
FIG. 1 depicts an overview of a fluid administration set interconnecting a medical fluid reservoir with a patient, the administration line of the set having a drip chamber located at the downstream end of a burette with an electret enhanced automatic shut off valve formed as an integral part of the drip chamber.

Referring now to the drawings with more particularity, wherein like reference numerals in the separate views refer to like or corresponding elements, there is shown in FIG. 1 an overview diagram of a medical fluid administration system 20 terminating in the vein of the arm of a patient 22. A medical fluid reservoir 24 is hung on a standard hanger 26, only a part of which is shown, above the level of the patient 22 so that a gravity feed system is provided in this embodiment. The reservoir in this case includes a flexible bag, however, a bottle or other type of container could also be used. An access device 28 penetrates the stopper or septum of the bag to establish fluid communication between the bag and upstream tubing 30 of the fluid administration system. In this case, a medical fluid administration set 34 is used and includes the access device, the upstream tubing, a burette 36, a drip chamber 38 with an automatic shut off valve, downstream tubing 40, and a connection device 42 for a sharpened cannula (not shown) used to penetrate the patient's vein and establish fluid communication with his or her circulatory system. The bag access device 28 may take the form of a sharpened and vented spike that penetrates a closure of the bag in this embodiment. Thus, medical fluid 32 within the bag is conducted to the patient 22 through the administration set 34.

Figure 2:
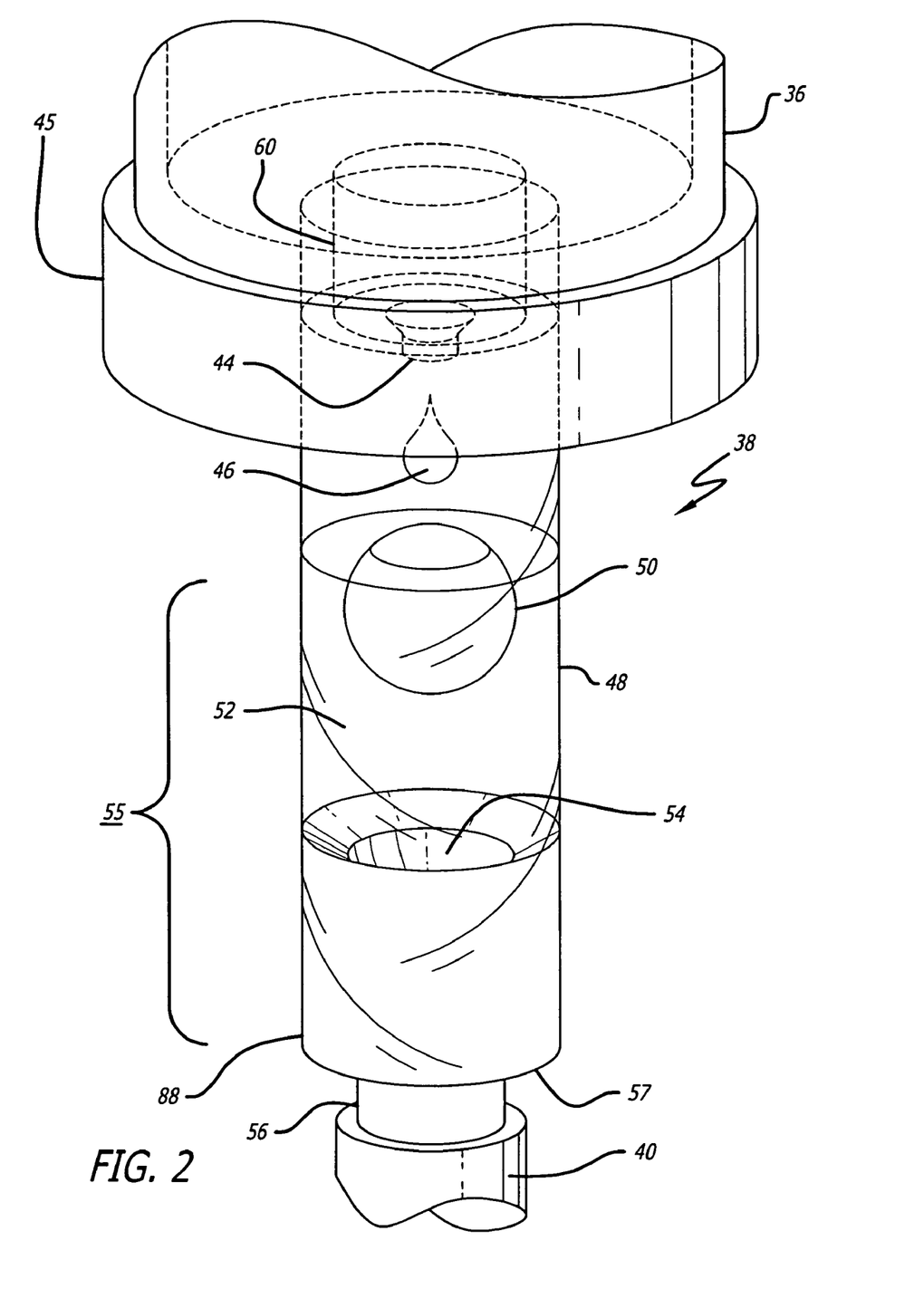
FIG. 2 depicts a partially cutaway, perspective view of a drip chamber mounted at the downstream end of a burette, with a float suspended in the medical fluid of the drip chamber.

FIG. 2 is a perspective view of one embodiment of the drip chamber 38 that includes the use of an electrical field to attract the valve components together to increase the shut off force of the valve. An electrical attractive force is generated by non-magnetic and non-metallic components. In this embodiment, at least one electret is used to form the shut off valve 55. As shown, the drip chamber is mounted to the downstream end of the burette 36 for this application although this is not required. In another embodiment, the drip chamber may instead have a sharpened spike or other device at its upstream end for directly accessing the medical fluid reservoir 24. Such configurations for drip chambers are common. Additionally, in this embodiment, the electret enhanced automatic shut off valve is located in the drip chamber. However, the electret enhanced valve could be used in other fluid containers or conduits as well.

The drip chamber 38 includes a precise drop former 44 located at its upstream or proximal end 45 operating to form drops 46 of a known size from the fluid in the burette 36 and permit those drops to fall into the transparent container 48 of the drip chamber. A stop member, in this embodiment a float 50, is floating in the medical fluid 52 of the transparent container due to its buoyancy. Downstream of the float is a valve seat 54 in which the float will seat when the fluid level within the container lowers sufficiently. The float and the valve seat form the two components of the shut off valve in this embodiment. In accordance with an aspect of the invention, at least one of the float and the valve seat is formed of an electret or other non-magnetic and non-metallic material that has an electrical charge that creates an electrical field to attract the other component of the valve. The other component of the valve in this embodiment is formed of a non-magnetic and non-metallic material, such as a dielectric, that is attracted by the electrical field created by the other component of the same valve. Because of this electrical field, the float and the valve seat are attracted together to shut off flow through the drip chamber. In another embodiment, both the float and the valve seat are formed of electrets having opposite electrical charges to attract the two valve components together.

The fluid level in the drip chamber will vary depending on the amount of fluid remaining in the reservoir 24, in the upstream tubing 30, and in the burette (see FIG. 1). As the level of fluid 52 in the drip chamber decreases, the float will approach closer and closer to the valve seat, eventually seating itself in the seat and shutting off fluid flow through the drip chamber. The drip chamber also includes a downstream or distal end 57 and defines an exit orifice 56 or outlet port at the downstream end to which the downstream tubing 40 is attached in this embodiment. When the float is seated in the valve seat, the electret enhanced shut off valve 55 stops all flow of fluid, including air, from the drip chamber into the tubing 40. Also in this embodiment, the material used to form the transparent container of the drip chamber is also used to form the exit orifice, although other arrangements may be used.

In the operation shown in FIGS. 1 and 2, fluid from the reservoir 24 flows through the upstream tubing 30 and into the burette 36 where it is accumulated to the desired level. The inlet to the burette is then closed and the fluid exits through an exit port 60 of the burette into the drop former 44 of the drip chamber 38. The drop former forms precisely-sized drops that may be counted and timed to verify that a desired flow rate has been established with a variable clamp or other means (not shown). When the fluid level in the transparent container 48 is high, the float 50 floats near the upper surface of the fluid in the container and is above the valve seat 54, thereby allowing fluid to flow out the exit orifice 56 of the drip chamber and through the downstream tubing 40 into the patient 22 (FIG. 1).

Figure 3:
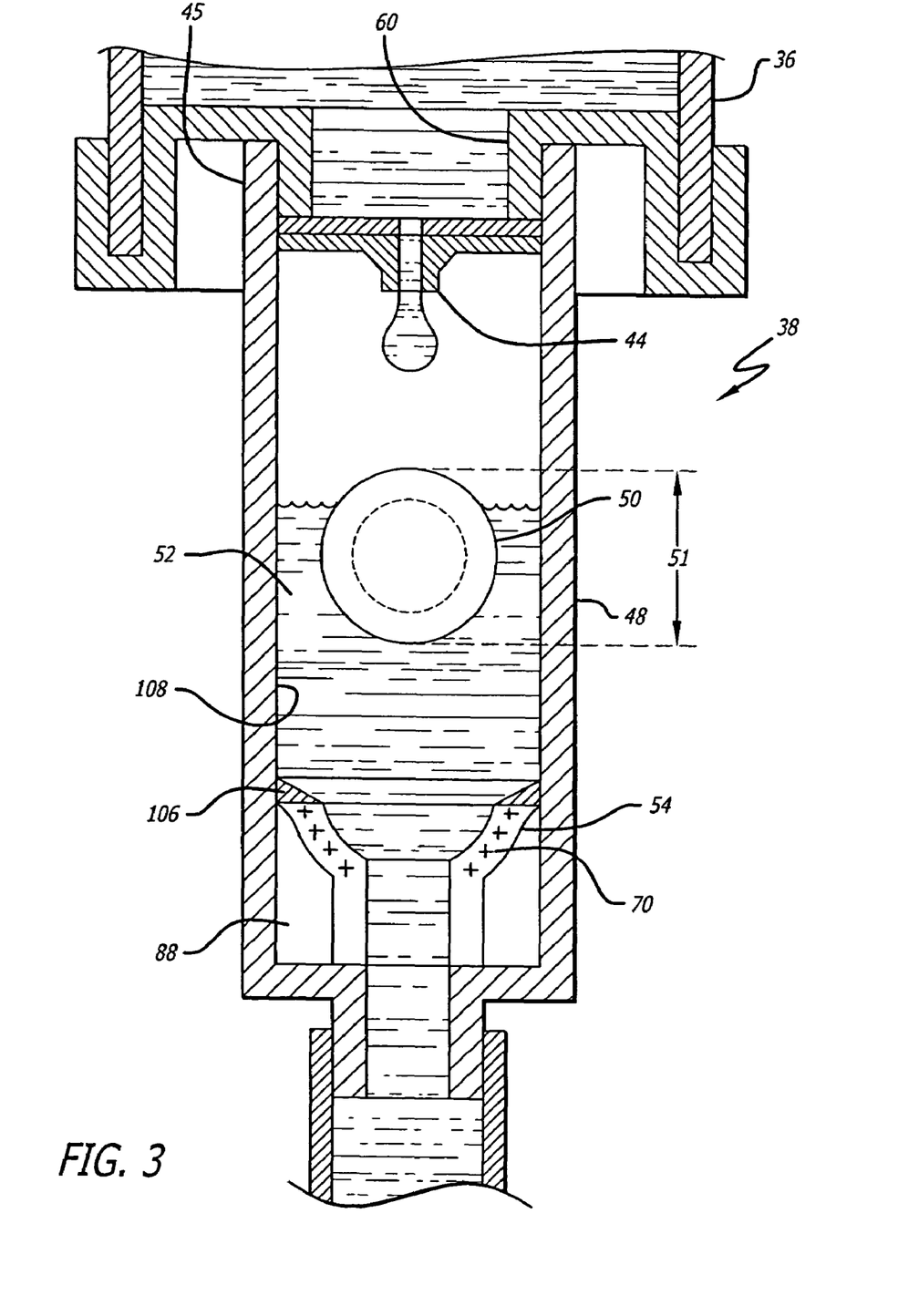
FIG. 3 depicts a cross-sectional view of the electret enhanced automatic shut off valve shown in FIG. 2 with the buoyancy of the float causing it to float near the surface of the medical fluid in the container, and showing that the valve seat includes an electrical charge that attracts the dielectric float into engagement with the valve seat to shut off flow of the medical fluid from the drip chamber.

Referring now to FIG. 3, the elements of FIG. 2 are shown in cross-sectional form. More detail is also shown of the downstream end 57 of the burette 36. The upstream or proximal end 45 of the drip chamber 38 is connected, in this embodiment, directly to the output, or downstream end 60 of the burette 36. The float 50 is shown suspended in the fluid 52 of the drip chamber above the valve seat 54 due to the relatively high level of the fluid and the buoyancy of the float. The float, as shown in cross-section, defines a sphere or ball-shaped body. In other embodiments, the float or stop member may be oblong, and may take on a variety of shapes, including elliptical, cylindrical, conical, or any three-dimensional polygonal shape, such as a square, rectangle, or pyramid. It is important that the shape of the stop member complements the shape of the valve seat 54 in order to form a fluid tight seal when the stop member is seated in the valve seat. In this embodiment, the stop member is made of a dielectric, such as a nonpolar polymer. The density of the float should be less than the density of the fluid expected to be in the chamber. Typically, the density of the float may be modified by making the float hollow or impregnating the float with an inert gas.

The valve seat 54 in this embodiment is also made of a dielectric, such as a nonpolar polymer, such as a syndiotactic polystyrene (SPS) or a Teflon PTFE, formed into an electret having an electrical charge 70 permanently affixed in the bulk of the valve seat for attracting the float 50 to fully engage the valve seat and therefore into a sealing position in the valve seat to shut-off fluid flow. In another embodiment, the charge may be permanently affixed to the surface of the valve seat. In one embodiment, the valve seat has a rounded form for the seat that is complementary to that of the float to readily accommodate the round-shaped float. The configuration of the valve seat may need to be altered if the shape of the stop member or float is other than round.

Because the float 50 is formed of a dielectric and is attracted by the electrical field created by the electret valve seat 54, the float and valve seat will attract one another. The attractive force between the float and the valve seat need not be large. In one embodiment, the buoyancy of the float would be large enough to break the float loose from the valve seat when fluid is introduced in the drip chamber and the level of fluid rises. In another embodiment, the attractive force developed between the float and the valve seat is so high that the float must be manually dislodged from the valve seat before it will float to the surface of the fluid in the container of the drip chamber as shown in FIG. 3.

Figure 4:
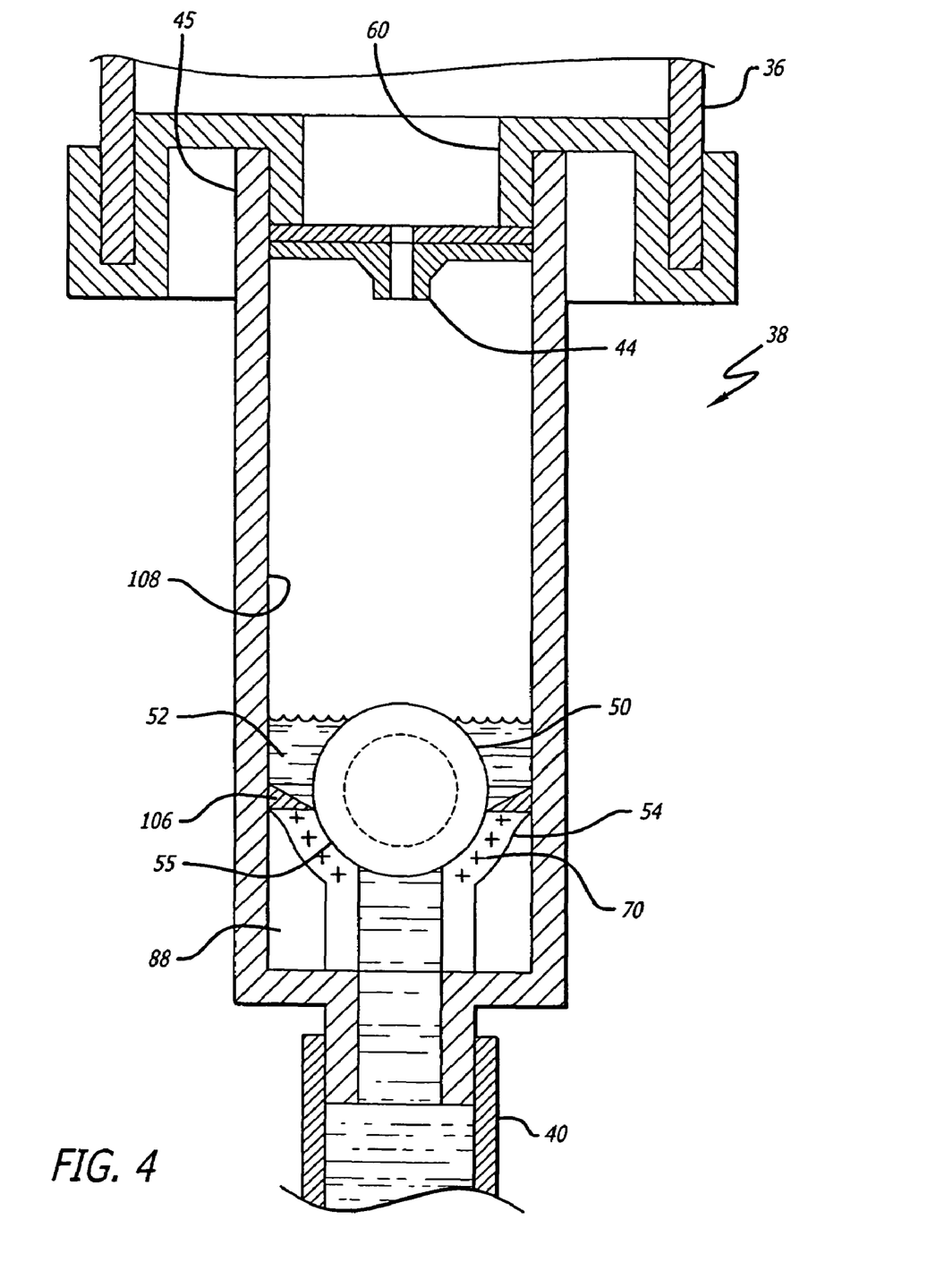
FIG. 4 depicts a cross-sectional view of the drip chamber shown in FIG. 3 with the float now fully engaged with the valve seat and thereby shutting off flow from the drip chamber, the electrical charge of the valve seat creating an electrical field that attracted the float into full engagement with the valve seat.

When a lowered level of fluid exists in the chamber, as shown in FIG. 4, the float is attracted into a fully engaged position with the valve seat at the bottom of the chamber. As the fluid level decreases to a predetermined amount or quantity, and hence the distance between the float and the valve seat 54 decreases, the attraction between the float and the valve seat created by the electrical field will overcome the buoyancy of the float in the fluid and cause the float to fully engage the valve seat thereby shutting off flow and sealing the system against the entry of air.

In one embodiment, to maximize pressure and create a gas tight seal, the float 50 has a radius of R, and the opening of the valve seat 54 has a radius of R minus some amount. However, the radius of the valve seat should not be too much smaller, so that the distance below the seal between the positively-charged float and the negatively-charged valve seat is minimized, thus maximizing the retention force of the seal. In this way, the force drawing the float into the valve seat is gravitational force plus the attraction created by the existence of the electrical field. In one embodiment, the round-shaped float has a radius of 0.559 cm, yielding a volume of 0.73 cm$^3$. It further has a weight of 0.62 g. Therefore, the float would have a density of 0.85 g/cm$^3$, which is enough to float the float when there is a liquid in the chamber with a density greater than 0.85 g/cm$^3$. Normal water having a density of approximately 1 g/cm$^3$ would cause the float in this embodiment to float away from the valve seat. Further to this embodiment, the opening of the valve seat has a radius of 0.45 cm and a radius of curvature of 0.50 cm. This prevents the float from falling through the opening of the valve seat and allows it to rest on the edge of the valve seat to form a seal when a decreased amount of fluid is in the drip chamber. This further minimizes the distance between the seal and the electrical charge located below the float in order to maximize the retention force of the seal.

It should be noted that the electrical charge 70 of the valve seat 54 may be physically isolated from direct contact with any medical fluid that flows through the drip chamber 38. By coating the valve seat with Parylene™ or other water resistant material to prevent fluids from reaching the electrical charges embedded in the valve seat, such fluid does not come into contact with the electrical charges.

In the embodiment shown in FIG. 3, the transparent container 48 portion of the drip chamber 38 is relatively full of fluid 52 and the float 50 is buoyed to the fluid surface. It should be noted that the float has a diameter, designated as 51, and that the bottom of the float is submerged with some volume of fluid 52 above it. Therefore when the submerged bottom of the float seats in the valve seat 54 shutting off fluid flow, the fluid above its position at the valve seat will remain in the drip chamber. This is shown in FIG. 4. As is apparent, the diameter 51 of the float (FIG. 3) has an effect on the amount of fluid remaining in the drip chamber when the electret enhanced automatic shut off valve 55 shuts off fluid flow and may be selected to result in a desired amount of fluid remaining.

The amount of fluid remaining in the drip chamber when shut off occurs can also be controlled by the strength of the electrical field attractive force developed by the electrical charge. The stronger the electrical field attractive force, the sooner the float 50 will overcome its buoyancy force and will be drawn through the remaining fluid in the drip chamber to seat in the valve seat 54, leaving more fluid remaining in the drip chamber than if the electrical field force were weaker. Thus, the strength of the electrical field force produced by the electrical charge attracting the float may be selected so that the charge will attract the float to the valve seat for shutting off fluid flow when a selected level of fluid remains in the container.

Similarly, the strength of the electrical field force produced by the charges may be selected so that the float will more readily align itself with the valve seat for automatic shutoff when the container is disposed at an angle other than vertical. The electret enhanced automatic shut off valve 55 will therefore be effective under a wider range of conditions of use of the drip chamber 38 than otherwise. For example, even in the case of the drip chamber being used during transport of the patient where the drip chamber may experience widely fluctuating tilt angles, the electret enhanced automatic shut off valve 55 will continue to function properly due to the strength of the electrical field attraction forces between the components of the valve.

In this embodiment, it should be noted that because of the spherical shape of the float 50, the float cannot wedge itself within the transparent container 48 thereby rendering the valve, of which it forms a part, inoperative. Furthermore, an outer edge of the valve seat 54 may contain a downward taper 55 to guide the spherical float into a sealing position with the valve seat. Thus, the float cannot trap itself on the outer edge of the valve seat when the liquid level has decreased therefore eliminating another basis for valve inoperability.

As the fluid level 52 in the drip chamber 38 decreases, the float 50 will move closer and closer to the valve seat 54 until a point is reached where the electrical field attraction is greater than the upward force on the float caused by its buoyancy. At this point, the float will move into the position shown in FIG. 4 to seal off the fluid flow of the remaining fluid 52 from the drip chamber 38 through the exit orifice 56. Because the float seats in the valve seat and seals the drip chamber before the fluid in the chamber is depleted, it prevents the entry of air into the downstream tubing 40. A beneficial effect is that the drip chamber 38 and downstream tubing remain primed.

The valve seat 54 includes a cylindrically-shaped base 88 that has an outer diameter equal to or just smaller than the inner diameter of the transparent container 48, so that it may be slid into place within the container. The cylindrically-shaped base may be held in place with adhesive, a snap fit, or other means, as will be discussed below in more detail. However, it should be noted that in this embodiment, the base 88 must make enough contact with the transparent container 48 portion of the drip chamber 38 so that the fluid in the chamber cannot flow around the outside of the base between it and the drip chamber and out the exit orifice 56 to thereby compromise the valve 55.

With continuing reference to the embodiment of FIGS. 3 and 4, the base 88 in this embodiment includes a locking ring 106 formed on the inner wall 108 of the transparent container 48. The locking ring is ramped inwardly towards the downstream direction but is perpendicular to the wall 108 in the upstream direction. The base 88 may be slid into the transparent container 48 from the proximal end 45 of the chamber and over the locking ring during assembly, and the base will be held in position as shown in FIGS. 3 and 4 by the locking ring. The locking ring 106 may be a part of the transparent container part of the drip chamber or may be a separate piece added to the transparent container and held in place through adhesive or other means.

In use, operation of the electret enhanced automatic shut off valve 55 may commence with the fluid reservoir 24 being accessed and the administration set 34 primed. A selected amount of fluid is allowed to flow into the burette 36. The burette is then closed and fluid is permitted to flow from the burette exit port 60 into the drip chamber 38. With little fluid initially in the drip chamber, the float 50 will be in a sealing position with the valve seat 54. However, as the fluid level rises in the drip chamber, the selected buoyancy of the float will eventually overcome the electrical field attraction between the seated float and the valve seat, causing the float to dislodge from the valve seat and buoy to the surface of the fluid away from the valve seat. In other embodiments, the float may be removed from its sealing position with the valve seat by mechanical means, such as by squeezing the side of the transparent container 48 at the valve seat, thereby overcoming the forces holding it in a sealed position in the seat. Once the float rises with the fluid level in the drip chamber, the exit orifice 56 opens so that fluid may flow to the patient 22. As the measured amount of fluid in the burette is exhausted, the fluid level in the drip chamber will become depleted and the electrical field attraction between the first and second electrical charges 66 and 70 will cause the float to seal off the exit orifice of the drip chamber and flow through the fluid administration set 34 will cease. Because of the spherical shape of the float in this embodiment, it will not become wedged in the transparent container of the drip chamber even if the drip chamber is not level or is being moved due to patient activity or transport. Additionally the float, formed of a dielectric that is attracted by the electrical field, will strongly be attracted into proper alignment with the negatively-charged valve seat. Furthermore, the downwardly tapered outer edge of the valve seat will help guide the float into contact with the valve seat. The float's spherical shape also assists in properly locating it in the valve seat. As a result, the prime in the fluid administration set is preserved and this feature of the automatic stop-valve 55 will allow the burette to be refilled with fluid and an infusion to begin again without having to re-prime the administration set.

Figure 5:
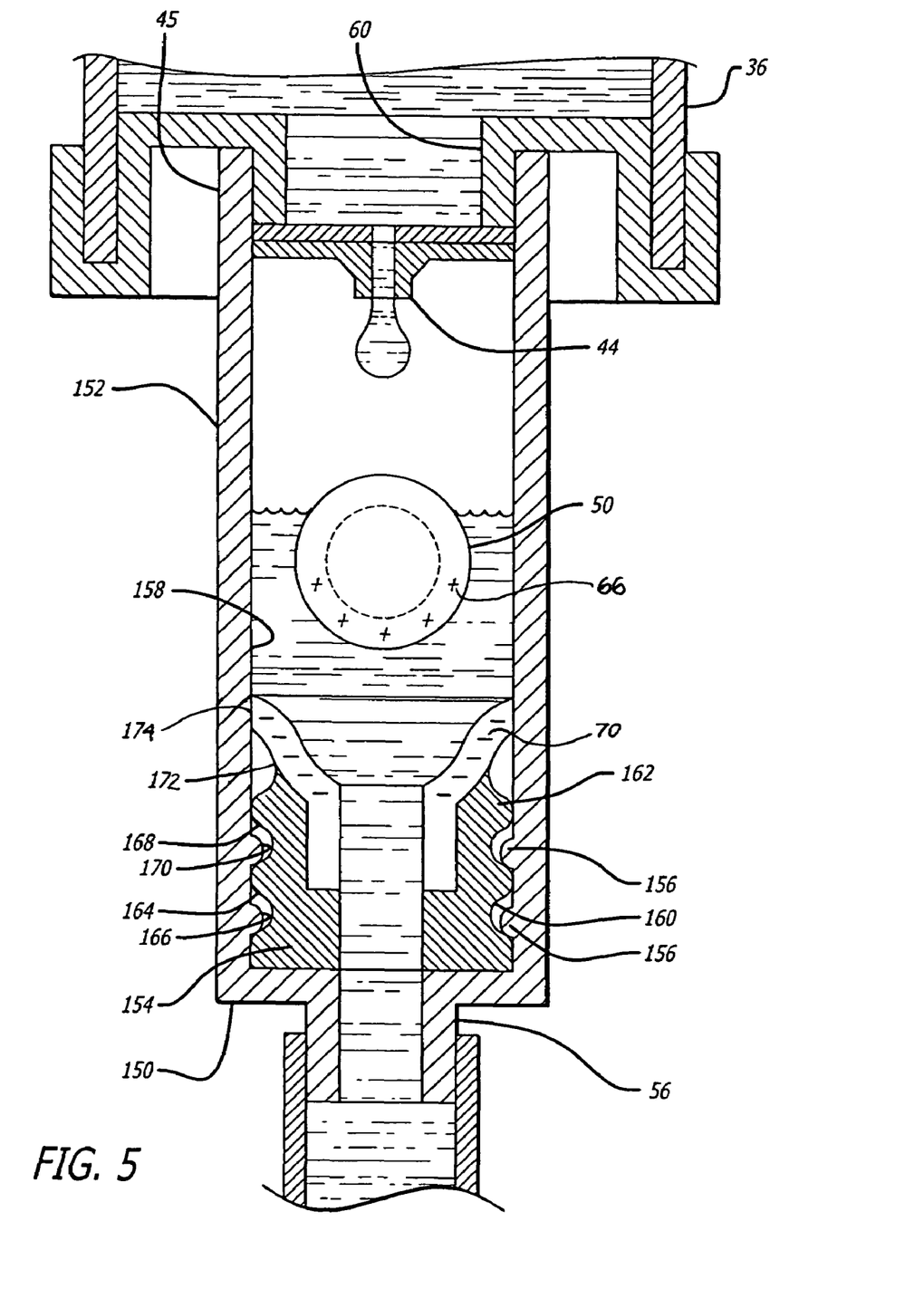
FIG. 5 depicts a cross-sectional view of a drip chamber in which details of an embodiment of a valve seat mounting arrangement are shown, as well as both the float and the valve seat having opposite charges to create electrical fields that attract the float and the valve seat together to shut off flow from the drip chamber.

Referring now to FIG. 5, a cross sectional view of another embodiment of a drip chamber 152 is shown. A valve seat 154, seal, and retaining arrangement is shown including inward protrusions 156 from the inner wall 158 of the drip chamber with selectively located grooves 160 formed in the outer surface 162 of the valve seat 154. A first distal groove 164 is formed in the valve seat that coincides with a first protrusion 166 on the inner wall of the drip chamber. This, along with a second groove 168 on the valve seat and a second protrusion 170 on the wall 158 serve to engage two protrusions from the drip chamber wall and retain the valve seat 154 in the desired position in the drip chamber. The protrusions from the drip chamber wall take the form of rings in this embodiment. The grooves of the valve seat are also formed completely around the valve seat so that ease in manufacturing results. With such an arrangement, the valve seat can be inserted in any rotational position during assembly in manufacturing and will function perfectly. More or fewer protrusions and grooves may be used in other embodiments and they may take different shapes.

In FIG. 5, a third groove 172 formed at the proximal end of the valve seat leaves a raised ring 174 on the valve seat that will contact the inner wall 158 of the drip chamber and form a fluid seal. This fluid seal will prevent fluid from flowing around the outside of the valve seat and through the exit orifice 56.

Also in the embodiment of FIG. 5, both the float 50 and the valve seat 54 have electrical charges. The float is shown as having a positive electrical charge 66 while the valve seat is shown as having the opposite electrical charge 70, in this case, a negative electrical charge. Both the float and the valve seat are electrets in this embodiment and both create electrical fields. Because the electrical fields are opposite in polarity, the two valve components, i.e., the float and the valve seat, attract one another into full engagement to shut off flow from the drip chamber 152.

Figure 6:
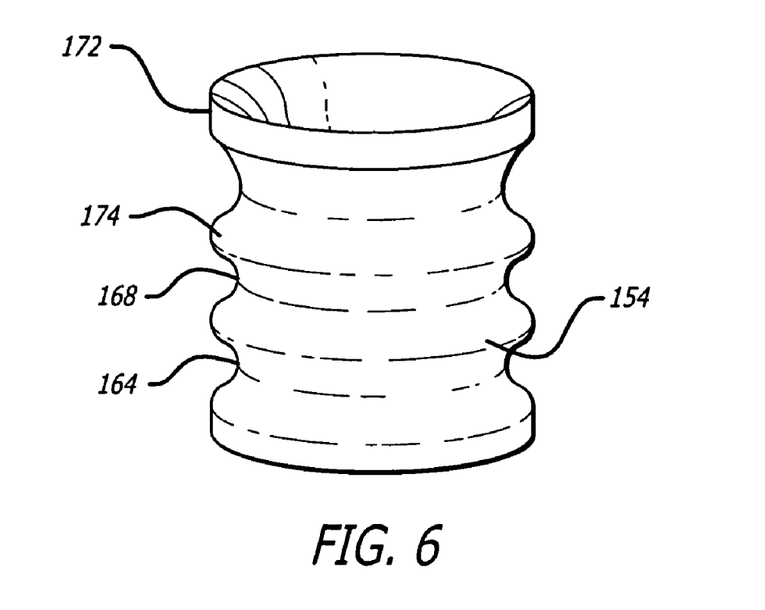
FIG. 6 depicts a perspective view of the outer surface of one embodiment of a valve seat.

FIG. 6 presents an external perspective view of the valve seat 154 of FIG. 5 showing the grooves 164 and 168. In a preferred embodiment, the drip chamber is tapered from a larger diameter at the upstream end to a smaller diameter at the downstream end. This arrangement will facilitate assembly of the valve seat in the drip chamber during manufacture. Additionally then, the valve seat will be tapered with a complementary taper and will snap over the protrusions 156 for permanent mounting in the drip chamber.

Figure 7:
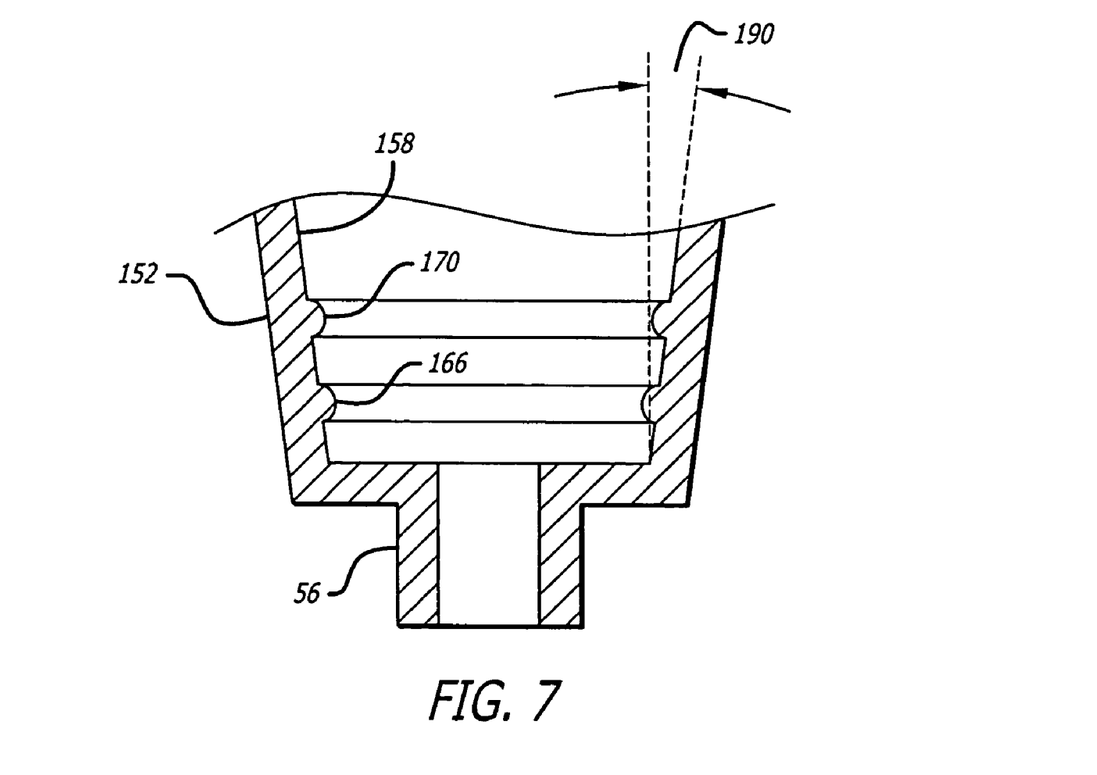
FIG. 7 depicts a partial schematic view of the downstream end of a drip chamber in which the valve seat of FIG. 6 may be mounted.

FIG. 7 shows in an exaggerated way the taper of the drip chamber 152 in one embodiment. The angle of taper is indicated by numeral 190. The taper not only aids in molding the drip chamber but also aids in inserting the valve seat 154.

A dielectric usable for the electret is a syndiotactic polystyrene (SPS) from Dow Plastics, Midland Mich., U.S.A. It is a nonpolar, non-metallic, and non-magnetic material that will function as an electret. Although the electrical field has been described above as being formed by an electret, other non-magnetic and non-metallic materials that can permanently hold an electrical charge may also be usable to accomplish the desired effects of the invention. For example, materials known as ferroelectric polymers may also function as non-magnetic, non-metallic materials that will permanently hold an electrical charge. Other materials that exist or that will be developed may also work well.

Thus there has been provided a new and improved medical valve device and method by which an attraction exists between the components that tends to close the valve, yet the attraction is generated by non-magnetic and non-metallic materials. Because of the use on non-magnetic materials, the valve in accordance with principles of the invention does not adversely affect an MRI environment and because non-metallic materials are used, there will be no interaction with medical fluids.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. An automatic shut off valve for use in regulating the flow of medical fluid from a medical fluid source, comprising:
    a container configured to operate in an upright position and to contain a varying level of medical fluid received from the medial fluid source and an amount of air above the received medical fluid, the container having an upstream end, a downstream end disposed below the upstream end, and an exit orifice formed at the downstream end through which the medical fluid exits the container, the upstream end and the exit orifice configured so that the received medical fluid will fill the container to a normal operating fluid level during the time that the medical fluid source contains medical fluid, and further configured so that the medical fluid in the container will decrease below the normal operating level during the time that the medical fluid source contains no further medical fluid;
    a valve seat disposed adjacent the exit orifice at the downstream end of the container and formed of a non-magnetic and dielectric material; and
    a stop member disposed and freely movable within the container having a buoyancy with which the stop member floats at the surface of the medical fluid in the container, the stop member being spaced apart from the valve seat when the medical fluid in the container has the normal operating level, the stop member formed of a non-magnetic and dielectric material;
    wherein at least one of the stop member and the valve seat comprises an electrical charge creating an electric field that attracts the other of the stop member and the valve seat and tends to move the stop member into sealing engagement with the valve seat to seal against fluid flow through the exit orifice;
    wherein the electric field has a strength selected such that, when the medical fluid in the container reaches a selected level that is more than empty but less than the normal operating level, the electric field overcomes the buoyancy of the stop member to move the stop member into sealing engagement with the valve seat, thereby preventing air above the medical fluid from flowing through the exit orifice.

2. The automatic shut off valve of claim 1 wherein both the stop member and the valve seat comprise electrical charges, each of which creates an electrical field that attracts each other tending to move the stop member and the valve seat into contact with each other.

3. The automatic shut off valve of claim 1 wherein the electrical charge is permanently affixed to the bulk of the at least one of the stop member and the valve seat.

4. The automatic shut off valve of claim 1 wherein the electrical field is produced as a result of the stop member comprising a first electrical charge and the valve seat comprising a second electrical charge, the first and second electrical charges being opposite and attracting each other.

5. The automatic shut off valve of claim 4 wherein both the first and second electrical charges are permanently affixed to the bulk of the stop member and the valve seat respectively.

6. The automatic shut off valve of claim 4 wherein both the first and second electrical charges are permanently affixed to the surface of the stop member and the valve seat respectively.

7. The automatic shut off valve of claim 1 wherein the material producing the electrical charge is disposed so that it does not have direct contact with medical fluid located in the container.

8. The automatic shut off valve of claim 1 wherein the at least one of the stop member and the valve seat that comprises an electrical charge that creates the electrical field comprises an electret.

9. The automatic shut off valve of claim 1 wherein both the stop member and the valve seat comprise an electret.

10. The automatic shut off valve of claim 1 wherein the at least one of the stop member and the valve seat that comprises an electrical charge that creates the electrical field comprises a ferroelectric polymer.

11. The automatic shut off valve of claim 1 wherein the stop member has a density that is less than a density of the fluid contained in the container whereby the stop member floats with the level of the medical fluid in the container.

12. The automatic shut off valve of claim 1 wherein the stop member and the valve seat comprise a nonpolar polymer.

13. The automatic shut off valve of claim 1 wherein the first electrical charge is permanently affixed to the surface of the at least one of the stop member and the valve seat comprising an electrical charge.

14. The automatic shut off valve of claim 1 wherein the downstream end of the container is tapered to guide the stop member toward the center of the valve seat.

15. The automatic shut off valve of claim 1 wherein the stop member is hollow.

16. The automatic shut off valve of claim 1 wherein the stop member includes an inert gas.

17. A method of automatically shutting off flow of medical fluid from a container having an upstream end and a downstream end with an exit orifice and a valve seat at the downstream end and a float located within the container that has sufficient buoyancy to float in the medical fluid and having a size selected to stop flow through the exit orifice when fully engaged with the valve seat, said method comprising:

producing a non-magnetic electrical field from at least one of the float and the valve seat;

forming both the float and the valve seat from a non-magnetic dielectric material that is attracted by the electrical field;

filling the container with medical fluid to a normal operating level with air above the medical fluid at which normal operating level the float floats at a position away from the valve seat and is therefore not engaged with the valve seat;

reducing the medical fluid in the container to a selected level that is more than empty and less than the normal operating level; and     when the medical fluid reaches the selected level, overcoming the buoyancy of the float by the attraction created with the electrical field so as to cause the float to be fully engaged with the valve seat thereby shutting off flow of the medical fluid through the exit orifice and preventing the air above the medical fluid from flowing through the exit orifice.

18. The method of automatically shutting off flow of claim 17 further comprising the step of permanently affixing an electrical charge to the bulk of at least one of the float and valve seat.

19. The method of automatically shutting off flow of claim 17 wherein the step of forming both the float and valve seat of a non-magnetic, non-metallic, dielectric material comprising forming at least one of the float and valve seat of a nonpolar polymer that is attracted by an electrical field.

20. The method of automatically shutting off flow of claim 17 wherein the step of producing an electrical field from at least one of the float and valve seat comprises forming the at least one of the float and valve seat from an electret.

21. The method of automatically shutting off flow of claim 17 wherein the step of producing an electrical field from at least one of the float and valve seat comprises forming the at least one of the float and valve seat from a ferroelectric polymer.

22. The method of automatically shutting off flow of claim 17 further comprising the step of selecting the strength of the electric field to keep the stop member in sealing engagement with the valve seat when the medical fluid in the container decreases below the normal operating level and after the medical fluid in the container returns to the normal operating level.

23. The method of automatically shutting off flow of claim 17 further comprising selecting the strength of the electric field to maintain the float fully engaged with the valve seat to prevent flow through the exit orifice even when refilling the container with the medical fluid to the normal operating level after reducing the medical fluid in the container to the selected level.

24. The method of automatically shutting off flow of claim 23 further comprising manually dislodging the float from the valve seat to allow it to float to the refilled level of medical fluid in the container after keeping the float fully engaged with the valve seat with the electric field.

\* \* \* \* \*